United States Patent [19]

Ritter et al.

[11] 4,455,309
[45] Jun. 19, 1984

[54] HALOMETHYL-THIOAMINO-BENZAMIDES, A PROCESS FOR THEIR PREPARATION AND THEIR USE

[75] Inventors: Helmut Ritter; Wilfried Paulus, both of Krefeld; Engelbert Kühle, Bergisch-Gladbach; Hermann Genth, Krefeld, all of Fed. Rep. of Germany

[73] Assignee: Bayer Aktiengesellschaft, Leverkusen, Fed. Rep. of Germany

[21] Appl. No.: 294,694

[22] Filed: Aug. 20, 1981

[30] Foreign Application Priority Data

Sep. 9, 1980 [DE] Fed. Rep. of Germany ....... 3033863

[51] Int. Cl.³ ................. A61K 31/495; C07D 241/04; A01N 47/08
[52] U.S. Cl. .................... 424/250; 544/387; 560/125; 562/432; 564/102; 564/142; 564/143; 564/153; 564/154
[58] Field of Search .......... 544/387; 424/250

[56] References Cited

U.S. PATENT DOCUMENTS 3,318,876 5/1967 Cignarella et al. ................ 544/386
3,453,244 7/1969 Preston ............................ 544/387

FOREIGN PATENT DOCUMENTS 1543614 3/1975 Fed. Rep. of Germany.

Primary Examiner—Alton D. Rollins
Assistant Examiner—James H. Turnipseed
Attorney, Agent, or Firm—Sprung, Horn, Kramer & Woods

[57] ABSTRACT

New halo-methyl-thioamino-benzamides of the formula

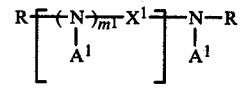

wherein
$X^1$ represents optionally substituted alkylene, arylene or alkarylene, it being possible for the alkylene and/or arylene and/or alkarylene groups to be linked via oxo, thio, carboxo, carboxamido or sulphoxo groups,
$A^1$ denotes the radical

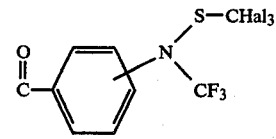

wherein
Hal represents halogen,
the various substituents R can be identical or different and represent hydrogen, optionally substituted alkyl or aryl or a substituted R, in the case where $X^1$ denotes optionally substituted ethylene and $m^1$ and $n^1$ represent the number 1, forms an ethylene bridge by being linked to a second R,
$m^1$ denotes an integer from 1 to 5 and indicates the number of linkages of

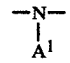

with $X^1$, and
$n^1$ denotes a number from 1 to 100;

a process for preparing the same by reaction of a halomethyl-thioamino-benzoic acid fluoride with an amine in the presence of a base and the use of such halo-methyl-thioamino-benzamides as microbicidal agents.

7 Claims, No Drawings

HALOMETHYL-THIOAMINO-BENZAMIDES, A PROCESS FOR THEIR PREPARATION AND THEIR USE

The invention relates to new halomethyl-thioamino-benzamides, a process for their preparation and their use in microbicidal agents.

The new halo-methyl-thioamino-benzamides are characterized by the formula

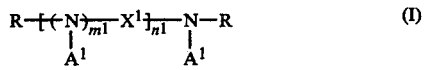    (I)

wherein
X$^1$ represents optionally substituted alkylene, arylene or alkarylene, it being possible for the alkylene and/or arylene and/or alkarylene groups to be linked via oxo, thio, carboxo, carboxamido or sulphoxo groups,
A$^1$ denotes the radical

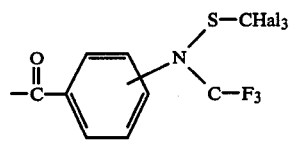

wherein
Hal represents halogen,
the various substituents R can be identical or different and represent hydrogen, optionally substituted alkyl or aryl or a substituent R, in the case where X$^1$ denotes optionally substituted ethylene and m$^1$ and n$^1$ represent the number 1, forms an ethylene bridge by being linked to a second R,
m$^1$ denotes an integer from 1 to 5 and indicates the number of linkages of

with X$^1$, and
n$^1$ denotes a number from 1 to 100.

Alkylene can be a straight-chain, cyclic or branched divalent hydrocarbon radical with 2 to 13 carbon atoms. Examples of alkylene radicals which may be mentioned are ethylene, propylene, isopropylene, butylene, isobutylene, pentylene, isopentylene, hexylene, cyclohexylene, dicyclohexylenemethane and isohexylene. Preferred alkylene radicals are the ethylene and hexylene radicals.

Arylene can consist of 1 to 5 phenylene nuclei, which can either be linked in a linear manner or fused together. The following arylenes may be mentioned as examples: phenylene, diphenylene, triphenylene, anthraquinonene and naphthylene.

Preferred arylenes are phenylene, biphenylene and naphthylene.

Alkarylene is in general a radical formed by linking one or more, preferably one to five, alkylene radicals with arylene radicals, in which the alkylene radical consists of 1 to 6 carbon atoms and the arylene radical consists of 1 to 5 phenylene nuclei linked in a linear manner or fused together. The following alkarylenes may be mentioned as examples: methylphenylene, isopropylphenylene, 2,2-bis-phenylenepropane, 1,1'-bis-phenylenecyclohexane, diphenylenemethane, 3,3'-dichloro-4,4'-diphenylenemethane, triphenylenemethane and xylylene.

Preferred alkarylenes are methylphenylene, diphenylenemethane and 2,2-bis-phenylenepropane.

The abovementioned alkylene and/or arylene and/or alkarylene groups can also be linked via oxo, thio, carboxo, carboxamido or sulphoxo groups. In this context, the following radicals may be mentioned as examples: diphenylene ether, diphenylene ketone, diphenylene sulphide, diphenylene sulphoxide, diphenylene sulphone and N-phenylenebenzoylamide.

Preferred radicals are diphenylene ether and diphenylene sulphide.

Halogen in the halogenomethyl groups of radical A$^1$ is in general fluorine and/or chlorine. Examples of the radical A$^1$ which may be mentioned are trifluoromethyl, trichloromethyl, difluoro-chloromethyl and dichloro-fluoromethyl. Preferably, some Hal moieties are fluorine while others are chlorine.

Alkyl is in general a straight-chain or branched hydrocarbon radical with 1 to about 6 (lower alkyl) carbon atoms. Examples which may be mentioned are methyl, ethyl, propyl, isopropyl, butyl, isobutyl, pentyl, isopentyl, hexyl and isohexyl. Preferred alkyl radicals are methyl and ethyl.

Aryl in general consists of one or more, preferably up to 5, phenyl radicals linked in a linear manner or fused together. The following radicals may be mentioned as examples of aryl: phenyl, chlorophenyl, nitrophenyl, diphenyl, diphenylmethane and naphthyl.

Phenyl is the preferred aryl.

In the case where X$^1$ denotes ethylene and m$^1$ and n$^1$ represent the number 1, it is also possible for two radicals R to be linked to form an ethylene bridge and for a piperazine ring thus to be formed.

The radicals X$^1$, A$^1$ and R can also be substituted by customary radicals. In this context, the following radicals may be mentioned as examples: nitro, halogen, such as fluorine, chlorine, bromine and iodine, carboxylic acid amide, N-alkylcarboxylic acid amide with 1–6 C atoms, N-phenylcarboxylic acid amide, carboxylic acid ester with 1–6 C atoms, carboxylic acid, sulphonic acid, fluoroalkyl with 1–6 C atoms, cyano and methoxy.

Preferred halo-methyl-thioamino-benzamides which may be mentioned are the compounds of the formula

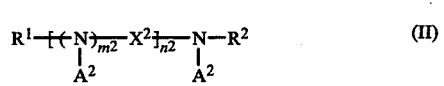    (II)

wherein
X$^2$ represents optionally substituted straight-chain or branched alkylene with 2 to 6 carbon atoms, arylene which has 1 to 5 phenylene nuclei linked in a linear manner or fused together, or alkarylene, it being possible for the arylene nuclei of the alkarylene to be linked by straight-chain or branched alkylene with 1 to 6 carbon atoms, and it being possible for the alkylene and/or arylene and/or alkarylene groups to be linked via oxo, thio, carboxo, carboxamido or sulphoxo groups,
A$^2$ denotes the radical

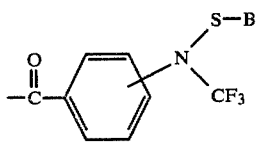

wherein
B represents trifluoro-methyl, trichloro-methyl, difluoro-chloro-methyl or dichloro-fluoromethyl,
$R^1$ and $R^2$ are identical or different and represents hydrogen, alkyl with 1 to 6 carbon atoms or aryl with 1 to 3 phenyl nuclei linked in a linear manner or fused together, or
$R^1$ and $R^2$, in the case where $X^2$ denotes ethylene and $m^2$ and $n^2$ represent the number 1, together also denote ethylene by being linked together, $m^2$ denotes a number from 1 to 5 and indicates the number of linkages of

with $X^2$ and
$n^2$ denotes a number from 1 to 20.
Halo-methyl-thioamino-benzamides of the formula

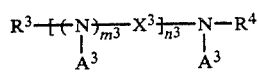   (III)

wherein
$X^3$ represents ethylene, hexylene, hexylene-2-carboxylic acid methyl ester, 2-methylphenylene, diphenylenemethane or diphenylenepropane, $A^3$ denotes the radical

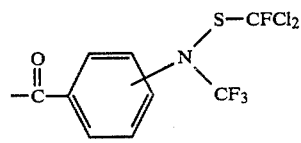

$R^3$ and $R^4$ are identical or different and denote hydrogen methyl or phenyl,
$m^3$ denotes the number 1 or 2 and indicates the number of linkages of

with $X^3$ and
$n^3$ denotes a number from 1 to 10, are particularly preferred.

The following halo-methyl-thioamino-benzamides may be mentioned specifically as examples: bis-N-(fluorodichloromethylthio)-N-(trifluoromethyl)-o-aminobenzoic acid piperazide, ethylenediamide; 2-methyl-1,5-phenylenediamide, and hexylene-2-(carboxylic acid methyl ester)-1,6-diamide; tris-N-(fluorodichloromethylthio)-N-(trifluoromethyl)-o-aminobenzoic acid 4,4',4''-triphenylenemethanetriamide; hexakis-N-(fluorodichloromethylthio)-N-(trifluoromethyl)-o-aminobenzoic acid pentaethylenehexamide; and bis-N-(fluorodichloromethylthio)-N-(trifluoromethyl)-m-aminobenzoic acid piperazide.

Furthermore, a process has been found for the preparation of fluoro- and chloro-methyl-thioaminobenzamides, which is characterized in that a fluoro- or chloro-methyl-thioamino-benzoic acid fluoride of the formula

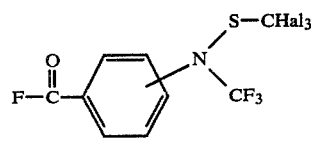   (IV)

wherein Hal has the abovementioned meaning, is reacted with an amine of the formula

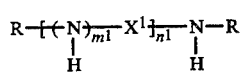   (V)

wherein $X^1$, R, $m^2$ and $n^1$ have the abovementioned meanings, at elevated temperature in the presence of a base.

Halo-methyl-thioamino-benzamides of the formula

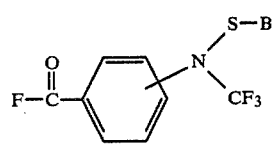   (VI)

wherein B has the abovementioned meaning, can preferably be employed for the process according to the invention.

Compounds of the following formula

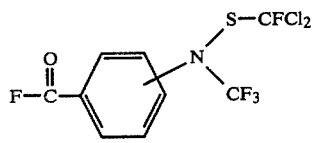   (VII)

become particularly preferred.

The meta- and ortho-isomers of the N-fluorodichloromethylthio-N-trifluoromethylaminobenzoic acid fluorides are in general employed.

The fluoro- and chloro-methyl-thioamino-benzoic acid fluorides are in themselves known, and can be prepared, for example, by reacting a N-trihalogenomethylaminobenzoyl fluoride with halogenomethanesulphonic acid chloride in the presence of a tertiary base, such as triethylamine (German Offenlegungsschrift No. 1,293,754).

The following fluoro- and chloro-methyl-thioaminobenzoic acid fluorides may be mentioned as examples: N-trichloromethylthio-N-trifluoromethyl-o-amino-benzoic acid fluoride; and N-trifluoromethyl-m-amino-benzoic acid fluoride.

Amines of the formula

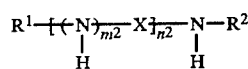   (VIII)

wherein $R^1$, $R^2$, $X^2$, $m^2$ and $n^2$ have the abovementioned meanings, can preferably be employed for the process according to the invention.

Amines of the following formula

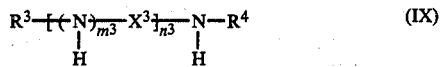 (IX)

wherein $R^3$, $R^4$, $X^3$, $m^3$ and $n^3$ have the abovementioned meanings, are particularly preferably employed.

The amines can be prepared in a manner which is in itself known (Houben-Weyl, Volume XI/1 (1957)). For example, they can be prepared by reaction of nitro compounds with reducing agents, by hydrogenation of nitrile groups, or by acid-catalysed polymerization of ethyleneimine.

The process according to the invention is in general carried out in the temperature range from $-20°$ C. to $100°$ C., preferably from $-10°$ to $+70°$ C.

In general, the process according to the invention is carried out under normal pressure. However, it is of course also possible to carry out the reaction under an increased pressure (for example up to 10 bars) or under reduced pressure (for example down to 0.1 bar).

Bases which can be employed for the process according to the invention are acid-binding agents which, under the reaction conditions, bond the hydrogen fluoride liberated. Examples which may be mentioned are alkali metal hydroxides and alkaline earth metal hydroxides, such as sodium hydroxide, potassium hydroxide, magnesium hydroxide and calcium hydroxide, alkali metal carbonates and alkaline earth metal carbonates, such as sodium carbonate, potassium carbonate, magnesium carbonate and calcium carbonate, ammonia and amines, in particular tertiary amines of the formula

 (X)

wherein $R^5$, $R^6$ and $R^7$ are identical or different and represent a lower straight-chain or branched alkyl radical (up to about 6 carbon atoms) or the phenyl radical.

Preferred bases are triethylamine and N,N-dimethylbenzylamine.

The process according to the invention can be carried out in a solvent and/or diluent. Solvents and/or diluents which may be mentioned are inert organic solvents which do not change under the reaction conditions. Toluene, dioxane, acetone, tert.-butanol or isopropanol may be mentioned as an example. It is also possible to carry out the process according to the invention in aqueous solution. The starting materials of the process according to the invention are in general employed in equivalent amounts. It is of course possible to employ one or other of the reactants in excess, for example an excess of up to 2 mols.

The solvent and/or diluent is in general employed in an amount of 20-80% by weight, relative to the fluoro- or chloro-methyl-thioamino-benzamide and to the amine.

The process according to the invention can be carried out, for example as follows:

The halo-methyl-thioamino-benzamide is diluted with a solvent, if appropriate, and is then added slowly to a homogeneous mixture of one mol of the amine, at least one mol of a base, and a solvent at the reaction temperature, whilst stirring. When the reaction has ended, the mixture is washed with water and the end product according to the invention is separated off.

The halo-methyl-thioamino-benzamides according to the invention can be used as active compounds for combating microorganisms, preferably in industrial materials, especially in non-living things.

Industrial materials with which the active compounds according to the invention are to be used to protect them from microbial change and destruction are, for example, adhesives, sizes, paper and cardboard, textiles, leather, wood, paints, plaster and plastic articles which can be attacked and/or decomposed by microorganisms.

Microorganisms which can cause degradation of or a change in the industrial materials are, for example, bacteria, fungi, yeasts, algae, mucilages and viruses. The fluoro- and chloro-methyl-thioaminobenzamides according to the invention are preferentially active against fungi.

Microorganisms of the following genera may be mentioned as examples: Coniophora, such as *Coniophora cerebella*, Lentinus, such as *Lentinus tigrinus*, Pullularia, such as *Pullularia pullulans*, Sclerophoma, such as *Sclerophoma pityophila*, Aspergillus, such as *Aspergillus niger*, Alternaria, such as *Alternaria tenuis*, Chaetomium, such as *Chaetomium globosum*, Polyporus, such as *Polyporus versicolor*, Penicillium, such as *Penicillium glaucum* and Trichoderma, such as *Trichoderma viride*.

The halo-methyl-thioamino-benzamides according to the invention can be converted into the customary formulations, such as solutions, emulsions, suspensions, powders, pastes and granules, depending on their field of application. The formulations can be prepared in a manner which is in itself known, for example by mixing the active compounds with an extender, with a liquid solvent and/or solid carriers, optionally with the use of surface-active agents, such as emulsifiers and/or dispersing agents, it being possible, for example in the case where aqueous extenders are used, for organic solvents optionally to be used as auxiliaries.

Liquid solvents for the active compounds can be, for example, alcohols, for example lower aliphatic alcohols, preferably ethanol and isopropanol, and aromatic alcohols, such as benzyl alcohol, liquid hydrocarbons, such as benzine fractions, chlorinated hydrocarbons, such as 1,2-dichloroethane, esters, such as diethylene glycol diacetate or ethyl acetate, ketones, such as cyclohexanone or acetone, or dimethylformamide or dimethylsulphoxide.

Solid carriers which are added during the preparation of the finished use forms of the active compound can be, for example, fine-particled aluminium oxides, silicates, carbonates, iron oxides, gypsum or wood flour.

Surface-active agents can be commercially available emulsifiers, such as aryl- and alkyl-sulphonates; ethoxylated alkylphenols, fatty acids, fatty alcohols or alkylamines; or dispersing agents, such as polycarboxylic acids, polyvinyl alcohol, lignin, sulphite waste liquors or methylcellulose.

The use form of the microbicidal agent according to the invention in general contains 0.1 to 95% by weight, preferably 0.5 to 90% by weight, of the halomethyl-thioamino-benzamide according to the invention as the active compound.

The amounts of active compound required for protecting industrial materials can be varied within relatively wide limits. In general, they are in the range from 0.0001 to 5% by weight, preferably in the range from 0.01 to 2% by weight, relative to the total amount of material to be protected.

The active compounds according to the invention can be present in the formulations as mixtures with other known inorganic and organic fungicides, bactericides and/or insecticides. The following active compounds may be mentioned as examples: benzimidazolylmethyl carbamate, tetramethyl-thiuramdisulphide, p-chloro-m-Cresol, 1-[-chlorophenyl-bis-(phenyl)-methyl]-imidazole, parathion and streptomycin.

A

Examples of the preparation of the halomethylthioaminobenzamides

General preparation instructions:

0.1 mol (34 g) of the N-(fluorodichloromethylthio)-N-(trifluoromethyl)-amino-benzoic acid fluoride, the ortho-isomers being designated A and the meta-isomers being designated B in the following table, are slowly added dropwise to a solution of 1 mol of an amine and 0.1 mol of triethylamine in 100 ml of p-butanol. The temperature thereby rises to about 30°–35° C. When the reaction has ended, the reaction mixture is poured into ice-water and filtered.

The compounds are summarized in the following table:

After the agar had solidified, the agar samples thus prepared were contaminated with pure cultures of various test fungi (see Table 2).

After storage of the agar at 28° C. and at a relative atmospheric humidity of 60 to 70% for two weeks, the samples were evaluated. Table 2 gives, as the minimum inhibitory concentration (MIC), the lowest concentration of a substance contained in an agar sample at which no growth of the species used took place at all.

TABLE 2

| Test organisms | MIC values of fluoro- and chloro-methyl-thioamino-benzamides in mg/1 according to Example No. | | | | | | |
|---|---|---|---|---|---|---|---|
| | 1 | 2 | 3 | 4 | 5 | 7 | 14 |
| Coniophora cerebella | 7.5 | 2 | 10 | 7 | 35 | 15 | 5 |
| Lentinus tigrinus | 75 | 20 | 50 | 50 | 100 | 35 | 5 |
| Pullularia pullulans | 150 | 75 | 1500 | 1500 | 750 | 1000 | 5 |
| Sclerophoma pityphila | 150 | 35 | 2000 | 75 | 150 | 200 | 5 |

What is claimed is:

1. A bis substituted piperazine compound of the formula

TABLE 1

| Example No. | Acid fluoride/amine | Name of compound | Melting point/°C. |
|---|---|---|---|
| 1 | A | Bis-N—(fluorodichloromethylthio)-N—(trifluoromethyl)-O—aminobenzoic acid 4,4'diphenylmethanediamide | 110 |
| 2 | A | Bis-N—(fluorodichloromethylthio)-N—(trifluoromethyl)-O—aminobenzoic acid ethylenediamide | 155 |
| 3 | A | Bis-N—(fluorodichloromethylthio)-N—(trifluoromethyl)-O—aminobenzoic acid 1,6-hexanediamide | 161 |
| 4 | A | Bis-N—(fluorodichloromethylthio)-N—(trifluoromethyl)-O—amino benzoic acid 2-methyl- 1,5-phenylenediamide | 175 |
| 5 | A | Bis-N—(fluorodichloromethylthio)-N—(trifluoromethyl)-O—aminobenzoic acid 1,4-piperazide | 180 |
| 6 | A | Bis-N—(fluorodichloromethylthio)-N—(trifluoromethyl)-O—aminobenzoic acid 4,4'-diphenylpropanediamide | 142 |
| 7 | A | Tris-N—(fluorodichloromethylthio)-N-13 (trifluoromethyl)-O—aminobenzoic acid diethylenetriamide | 122 |
| 8 | A | Bis-N—(fluorodichloromethylthio)-N—(trifluoromethyl)-O— 71 aminobenzoic acid hexylene-2-(carboxylic acid methyl ester)-diamine | |
| 9 | A | Hexakis-N—(fluorodichloromethylthio)-N—(trifluoromethyl)-O—aminobenzoic acid pentaethylenehexamide | 96 |
| 10 | A | Tris-N—(fluorodichloromethylthio)-N—(trifluoromethyl)-O—aminobenzoic acid 4,4'-4''-triphenylmethanetriamide | 130 |
| 11 | B | Bis-N—(fluorodichloromethylthio)-N—(trifluoromethyl)-m-aminobenzoic acid 4,4'-diphenylmethanediamide | 97 |
| 12 | B | Bis-N—(fluorodichloromethylthio)-N—(trifluoromethyl)-m-aminobenzoic acid 4,4'-diphenylpropanediamide | 96 |
| 13 | B | Bis-N—(fluorodichloromethylthio)-N—(trifluoromethyl)-m—aminobenzoic acid ethylenediamide | 75 |
| 14 | B | Bis-N—(fluorodichloromethylthio)-N—(trifluoromethyl)-m—aminobenzoic acid 1,4-piperazide | oil |

B

Microbicidal action of the fluoro- and chloro-methylthioamino-benzamides

EXAMPLE 15

Compounds according to the invention were incorporated, in each case in graduated concentrations between 1 and 5,000 mg/l for each test sample, into an agar which was prepared from beer wort and peptone.

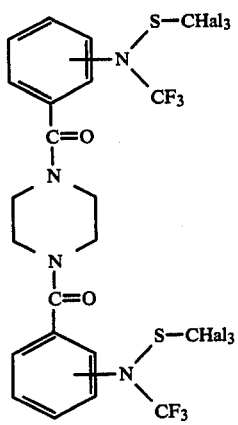

wherein Hal represents halogen.

2. A bis substituted piperazine according to claim 1 which is bis-N-(fluorodichloromethylthio)-N-(trifluoromethyl)-0-aminobenzoic acid-1,4-piperazide.

3. A bis substituted piperazine according to claim 1 which is bis-N-(fluorochloromethylthio)-N-(trifluoromethyl)-m-aminobenzoic acid-1,4-piperazide.

4. A microbicidal agent comprising the bis substituted piperazine of claim 1 in a microbicidally effective amount and a microbicidal diluent.

5. A microbicidal composition according to claim 4 wherein said bis substituted piperazine is present in an amount of 0.1 to 95% by weight based on the weight of the composition.

6. A process for protecting an industrial material against the action of a microorganism which comprises contacting said industrial material with a composition containing a bis substituted piperazine according to claim 1.

7. A process according to claim 6 wherein said industrial material is a non-living industrial material.

* * * * *

UNITED STATES PATENT AND TRADEMARK OFFICE
CERTIFICATE OF CORRECTION

PATENT NO. : 4,455,309
DATED      : June 19, 1984
INVENTOR(S): Helmut Ritter et al It is certified that error appears in the above-identified patent and that said Letters Patent is hereby corrected as shown below:

Col. 4, line 23 — Delete "$m^2$" and substitute --$m^1$--

Col. 7, Table 1, Ex. 7, 3rd Col. — After "-N-" delete "13"

Col. 7, Table 1, Ex. 8, 3rd Col. — After "-O- delete "71" and insert --71-- in last column Signed and Sealed this Nineteenth Day of February 1985

[SEAL]

Attest:

DONALD J. QUIGG

Attesting Officer — Acting Commissioner of Patents and Trademarks